(12) United States Patent
Yao

(10) Patent No.: US 9,022,762 B2
(45) Date of Patent: May 5, 2015

(54) ORTHOSIS MODIFICATION TOOL

(75) Inventor: Ninghua Yao, Durham, NC (US)

(73) Assignee: Beacon Innovations, LLC, Raleigh, NC (US)

( * ) Notice: Subject to any disclaimer, the term of this patent is extended or adjusted under 35 U.S.C. 154(b) by 246 days.

(21) Appl. No.: 13/543,318

(22) Filed: Jul. 6, 2012

(65) Prior Publication Data

US 2013/0009342 A1 Jan. 10, 2013

Related U.S. Application Data

(60) Provisional application No. 61/504,906, filed on Jul. 6, 2011.

(51) Int. Cl.
*B29C 53/80* (2006.01)
*A61F 5/01* (2006.01)

(52) U.S. Cl.
CPC ............. *A61F 5/0111* (2013.01); *A61F 5/0102* (2013.01)

(58) Field of Classification Search
USPC ................................... 425/2, 182, 403; 602/7
See application file for complete search history.

(56) References Cited

U.S. PATENT DOCUMENTS

| 5,897,515 | A | 4/1999 | Willner et al. | |
|---|---|---|---|---|
| 7,077,818 | B2 | 7/2006 | Ingimundarson et al. | |
| 7,815,587 | B2 | 10/2010 | Korner et al. | |
| 2003/0153852 | A1* | 8/2003 | Hinshon | 602/6 |
| 2005/0096576 | A1* | 5/2005 | Castro | 602/27 |
| 2008/0103423 | A1* | 5/2008 | Nieberding | 602/7 |

* cited by examiner

*Primary Examiner* — James Sanders
(74) *Attorney, Agent, or Firm* — Michael G. Johnston; Moore & Van Allen PLLC

(57) ABSTRACT

An apparatus is provided for mounting to a support for modifying an ankle-foot orthosis. The apparatus comprises a tooling device having a plurality of holes spaced over an outer surface of the tooling device. The tooling device includes a first portion having a longitudinal axis, and a second portion integral with the first portion and having a longitudinal axis substantially perpendicular to the longitudinal axis of the first portion. The second portion of the tooling device defines an opening for receiving the support. A peg is configured to be inserted into one of more holes of the tooling device. The peg comprises a body portion and a post depending from the body portion and configured to be received in the holes in the outer surface of the tooling device. In one embodiment, the body portion of the peg has a convex outer surface.

8 Claims, 7 Drawing Sheets

ORTHOSIS MODIFICATION TOOL

CROSS-REFERENCE TO RELATED APPLICATION

The present application claims priority to U.S. Provisional Application No. 61/504,906 filed on Jul. 6, 2011, the contents of the application is hereby incorporated by reference herein for all purposes.

BACKGROUND

An orthosis modification tool is described, and more particularly an orthosis modification tool used to create a depression or relief in an orthosis, or to reshape the inside surface of the orthosis.

An orthopedic brace is often referred to as an orthosis. An ankle-foot orthosis is worn on the lower leg and foot to support and align the ankle and foot. The object of the ankle-foot orthosis is to achieve a more natural and dynamic gait.

An ankle-foot orthosis comprises a shell of thin flexible, relatively rigid material. The shell at least partially extends around the periphery of the lower leg and includes a foot plate engaging the sole of the foot of the patient, thereby providing support for stabilizing and controlling motion of the ankle and foot. Fastening elements, such as straps, are provided and configured to wrap around the leg of a patient to secure the shell and foot plate to the leg and foot, respectively. The straps typically include hook-and-loop type fasteners mounted on overlapping portions of the fastening elements and the shell for an adjustable fit.

An ankle-foot orthosis is commonly formed from plastic materials, particularly thermoplastics such as polyethylene, polyurethane, polypropylene and the like. The flexibility of the material allows the orthosis to accommodate some fluctuation or change in the volume of the leg or foot by tightening or loosening the straps. The plastic orthosis may also be modified by trimming, sanding, grinding, buffing and shaping using a number of different types of tools. Some orthoses can even be cut by an ordinary pair of scissors for adjusting the height of the orthosis and the width of the foot-plate to, for example, accommodate the foot plate inside a shoe. The plastic material can also be heated and molded for further modification and a custom fit.

In use, the ankle-foot orthosis is in close contact with the lower leg, including sensitive areas such as the Achilles tendon, the heel and malleoli. Moreover, the width of the ankle and the size of the heel bone vary over a wide range as seen for a normal healthy population. Skin or tissue irritation is created by rubbing of the orthosis during movement or simply the static pressure on the tissue. Redness, swelling or blistering may develop in the irritated area.

Irritation from rubbing or pressure can be addressed by applying a soft padding on the inside of the orthosis. The orthosis can also be modified. Modification is typically accomplished by heating the orthosis for softening the plastic in the problem area. A tool is then used to create a depression in the hot plastic of the orthosis for creating space between inside surface of the orthosis and the location of the irritation of the patient. The ball end of a ball peen hammer is often used, as well as the end of a rivet bar, or any other tool that will create a depression. Unfortunately, this method is only crudely effective.

For the foregoing reasons, there is a need for an orthosis modification tool.

SUMMARY

An apparatus is provided for mounting to a support for modifying an ankle-foot orthosis. The apparatus comprises a tooling device having a plurality of holes spaced over an outer surface of the tooling device. The tooling device includes a first portion having a longitudinal axis, and a second portion integral with the first portion and having a longitudinal axis substantially perpendicular to the longitudinal axis of the first portion. The second portion of the tooling device defines an opening for receiving the support. A peg is configured to be inserted into one of more holes of the tooling device. The peg comprises a body portion and a post depending from the body portion and configured to be received in the holes in the outer surface of the tooling device. In one embodiment, the body portion of the peg has a convex outer surface.

A system is provided for modifying an ankle-foot orthosis. The orthosis modification system comprises a support and a tooling device having a plurality of holes spaced over an outer surface of the tooling device. The tooling device includes a first portion having a longitudinal axis, and a second portion integral with the first portion and having a longitudinal axis substantially perpendicular to the longitudinal axis of the first portion. The second portion of the tooling device defines an opening for receiving the support. A peg is configured to be inserted into one of more holes of the tooling device. In one embodiment, the opening in the second portion of the tooling device is configured to non-rotatably receive the support. In another embodiment, the opening in the second portion of the tooling device is configured to non-rotatably receive the support in a plurality of positions of the tooling device relative to the support.

A method of modifying an ankle-foot orthosis is also provided. The orthosis modification method comprises the steps of providing a tooling device having a plurality of holes spaced over an outer surface of the tooling device. The tooling device includes a first portion having a longitudinal axis, and a second portion integral with the first portion and having a longitudinal axis substantially perpendicular to the longitudinal axis of the first portion. The second portion of the tooling device defines an opening for receiving a support. Further steps of the method include sliding the tooling device onto the support, inserting a peg into a selected one or more of the holes in the outer surface of the tooling device, heating an area on a surface of the orthosis, and positioning the orthosis over the tooling device such that the heated area of the orthosis engages the peg for creating a depression or otherwise reshaping the inside surface of the heated area of the orthosis.

BRIEF DESCRIPTION OF THE DRAWINGS

For a more complete understanding of the present invention, reference should now be had to the embodiments shown in the accompanying drawings and described below. In the drawings.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise.

Figure 1:
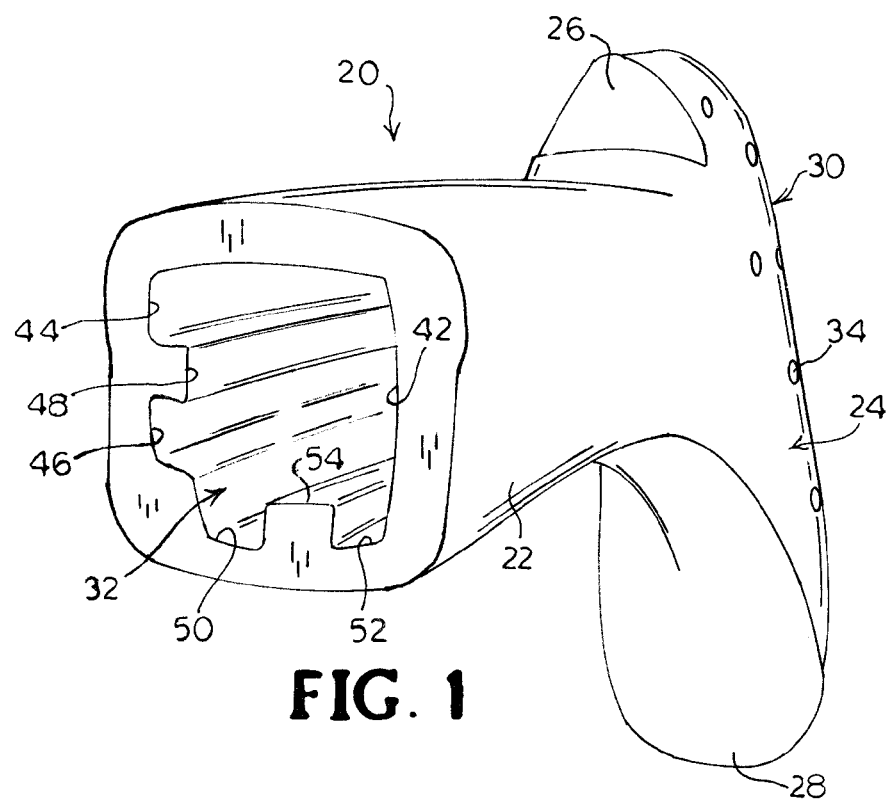
FIG. 1 is a perspective view of a tool for modifying an ankle-foot orthosis.
Figure 2:
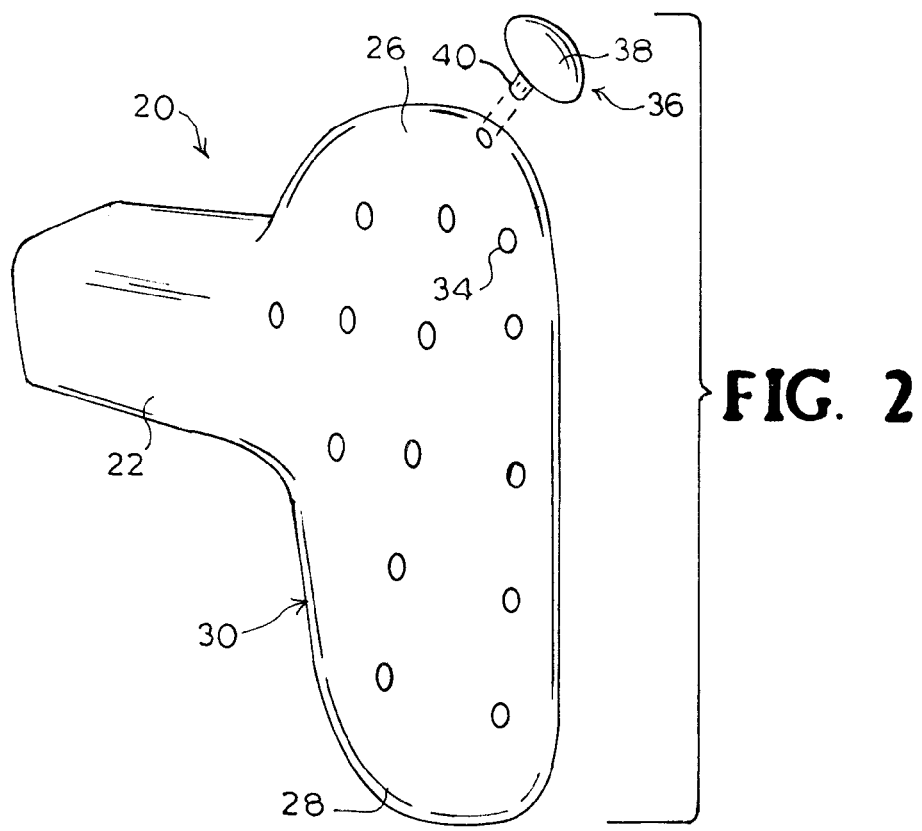
FIG. 2 is an exploded perspective view of the modification tool shown in FIG. 1 and a modification peg.

Referring now to the drawings, wherein like reference numerals designate corresponding or similar elements throughout the several views, an embodiment of a tool for modification of an orthosis is shown in FIG. 1 and generally designated at 20. The tool 20 is a rigid member formed in the shape of a lower leg 22 and foot 24 of suitable size, including a heel portion 26 and a toe portion 28 of the foot 24. The tool 20 is preferably comprised of a strong and stable metal alloy, such as stainless steel. Other suitable materials are those that are stable, strong and capable of withstanding significant multi-directional pressures and impact without fracture or distortion, including but not limited to urethanes, epoxies, plastics, composites, metal, metal alloys and the like. Nevertheless, the tool 20 can be constructed using a wide variety of materials. It is understood that the scope of the invention is not intended to be limited by the materials listed herein, but may be carried out using any materials that allow the construction and use of the described tool 20.

The tool 20 has an outer surface 30 and an inner region 32. The outer surface 30 of the tool 20 has a plurality of holes 34 spaced along the outer surface 30 for receiving a peg 36. In the embodiment shown, the peg 36 comprises a truncated hemispherical, or otherwise shaped, surface 38 that will allow the support or distribution of force needed to accomplish the desired modification. The peg 36 includes a post 40 extending from the flat surface of the peg 36. The holes 34 in the outer surface of the tool 20 are configured to receive the post 40 for securing the peg 36 on the tool 20.

The inner region 32 of the tool 20 defines a longitudinal generally rectilinear bore 42 therein. The bore 42 has a pair of spaced notches extending radially outwardly from the corners 44, 46 of one side edge 48 and another pair of spaced notches extending radially outwardly from the corners 50, 52 of a front edge 54 of the bore 42. Each of the notches 44, 46, 50, 52 along with at least a portion of the bore defines an opening for removably engaging a support, the combination thus forming a plurality of identically shaped support-engaging openings through the inner region of the tool 20, as will be described below. Each of the support-engaging openings extend nearly the full width of the tool 20 and are generally arcuate in shape with a slight outwardly radiused curvature. Each of the support-engaging openings for receiving the support includes one of the notches 44, 46, 50, 52, which generally corresponds to the shape and size of the edge of the support for preventing rotation of the tool 20 relative to the support. It is understood that although the FIGs. show four support engaging openings, a greater or lesser number of support-engaging openings could be used in other embodiments of the tool 20.

Figure 3:
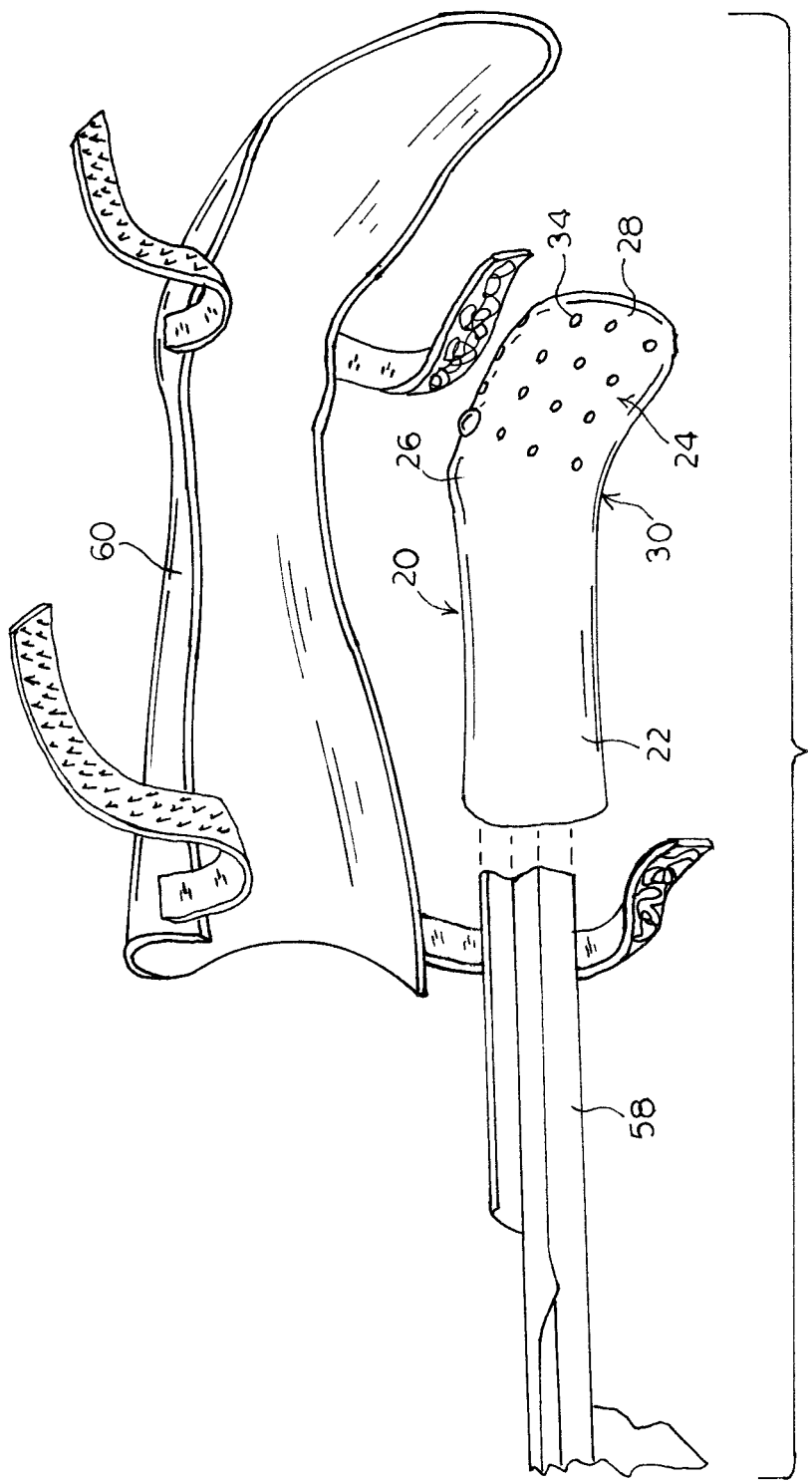
FIG. 3 is an exploded perspective view of an ankle-foot orthosis and the modification tool shown in FIG. 1 and in position for insertion of an end of a rivet bar.
Figure 4:
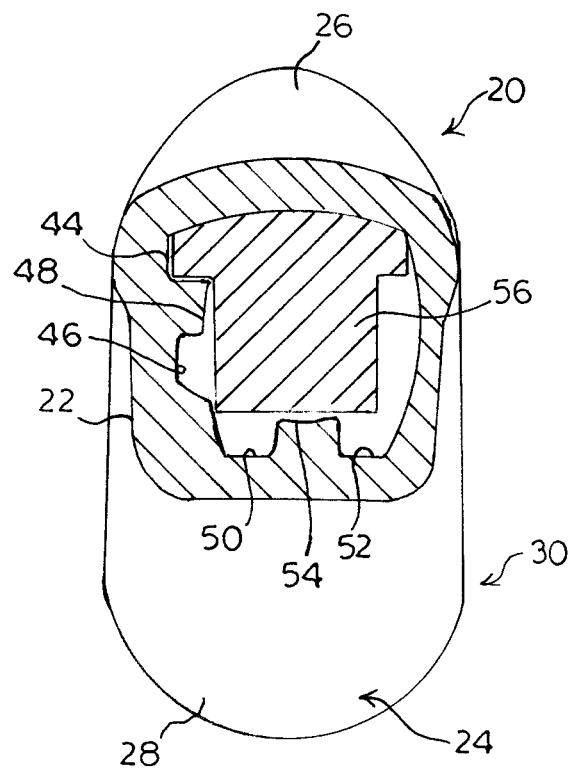
FIG. 4 is a transverse cross-section view of the modification tool in position on the rivet bar as shown in FIG. 2 with the modification tool in a first position relative to the rivet bar.
Figure 5:
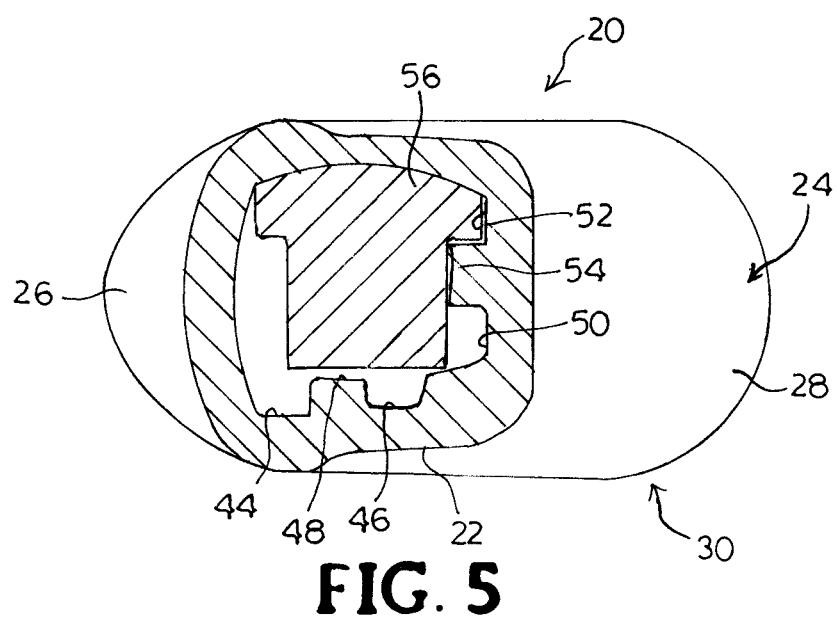
FIG. 5 is a transverse cross-section view of the modification tool in position on the rivet bar as shown in FIG. 4 with the modification tool in a second position relative to the rivet bar.
Figure 6:
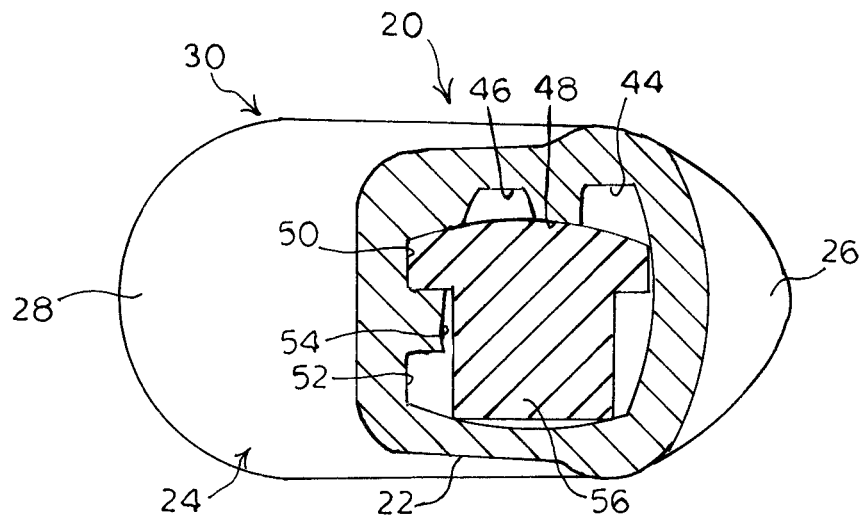
FIG. 6 is a transverse cross-section view of the modification tool in position on the rivet bar as shown in FIG. 4 with the modification tool in a third position relative to the rivet bar.
Figure 7:
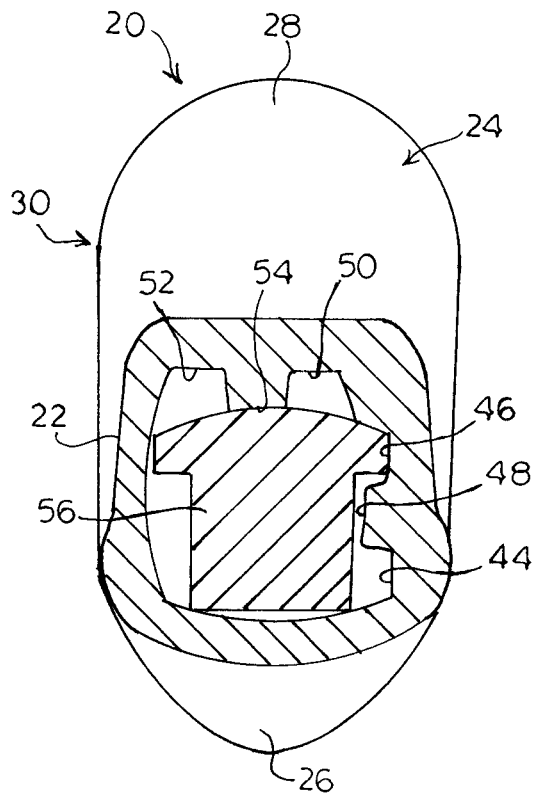
FIG. 7 is a transverse cross-section view of the modification tool in position on the rivet bar as shown in FIG. 4 with the modification tool in a fourth position relative to the rivet bar.

Referring now to FIG. 3, the tool 20 is shown with an anvil end 56 of a rivet bar 58 and an ankle-foot orthosis 60. Each of the plurality of support-engaging openings of the bore 42 in the leg portion 22 of the tool 20 is shaped to receive the anvil end 56 of the rivet bar 58. As shown in FIGS. 4-7, the notches 44, 46, 50, 52 of each of the four openings in the bore 42 facilitate sliding the tool 20 onto the bar 58 in four different positions: toe portion facing downwardly (FIG. 4), toe portion facing to the right (FIG. 5), toe portion facing to the left (FIG. 6), and toe portion facing upwardly (FIG. 7). The tool 20 is installed onto the bar 58 in a selected position by placing the leg portion 22 of the tool 20 adjacent the bar such that one of the support-engaging openings of the bore 42 is aligned with the anvil end 56 of the bar. The tool 20 is then pushed onto the bar 58 such that the anvil end 56 enters the support-engaging opening for securely holding the tool 20 on the bar.

Figure 8:
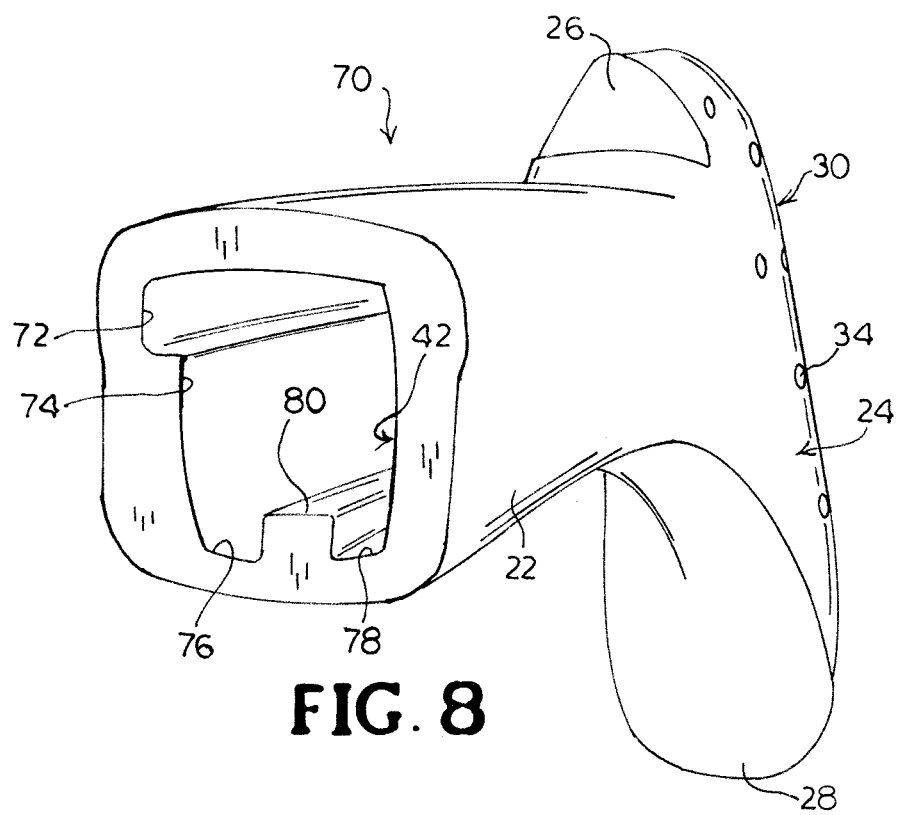
FIG. 8 is a perspective view of another embodiment of a tool for modifying an ankle-foot orthosis.
Figure 9:
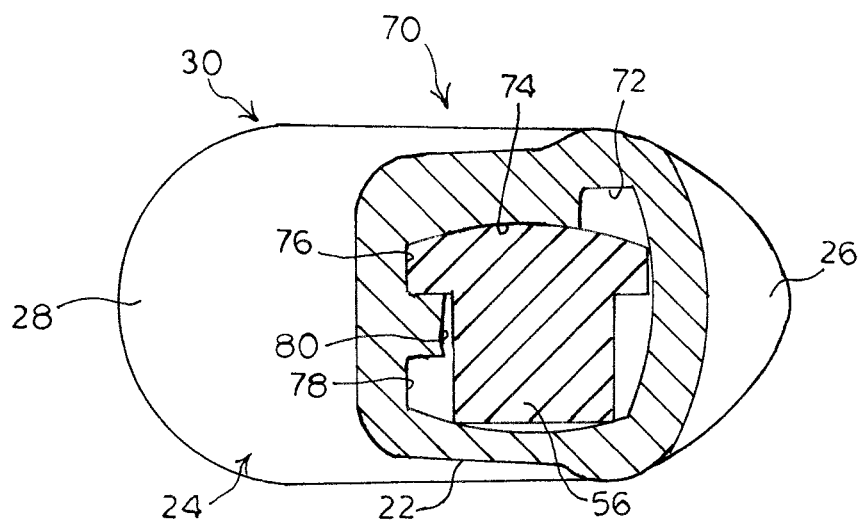
FIG. 9 is a transverse cross-section view of the modification tool in position on the rivet bar as shown in FIG. 8 with the modification tool in a first position relative to the rivet bar.
Figure 10:
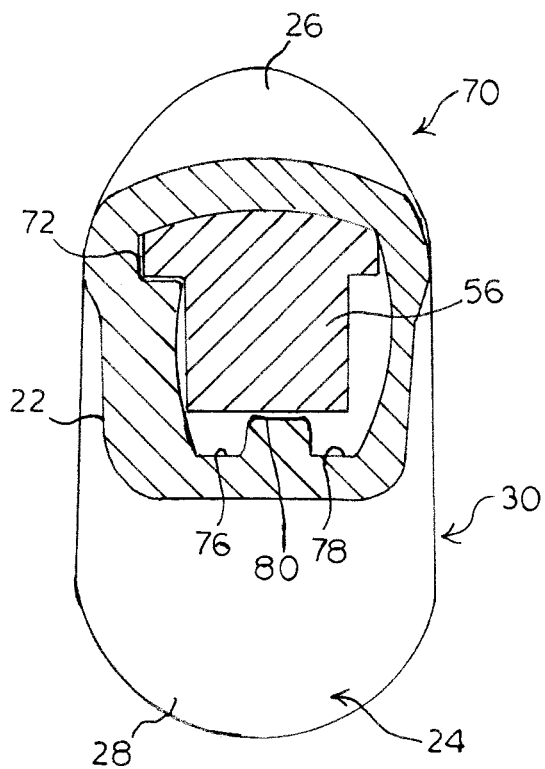
FIG. 10 is a transverse cross-section view of the modification tool in position on the rivet bar as shown in FIG. 9 with the modification tool in a second position relative to the rivet bar.
Figure 11:
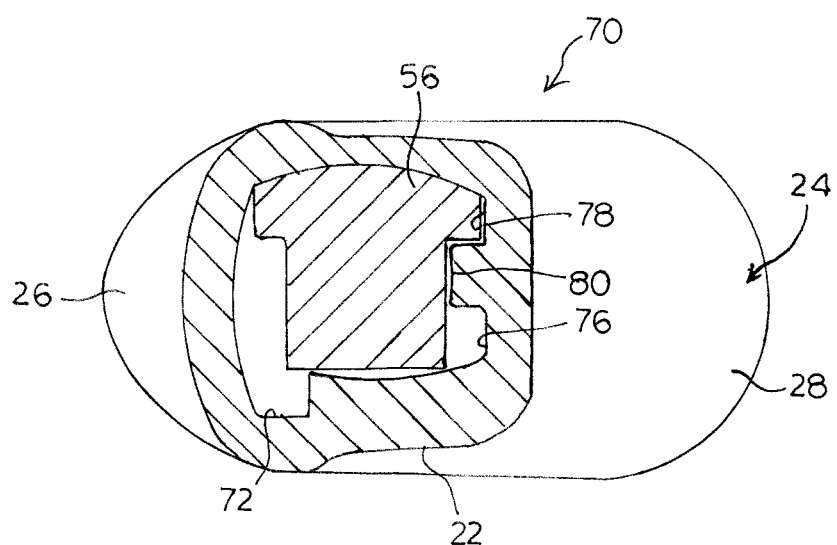
FIG. 11 is a transverse cross-section view of the modification tool in position on the rivet bar as shown in FIG. 9 with the modification tool in a third position relative to the rivet bar.

Another embodiment of a tool for modification of an orthosis is shown in FIG. 8 and generally designated at 70. Three support-engaging openings are provided in this embodiment of the tool 70. Specifically, the bore 42 has a single notch 72 extending radially outwardly from a corner of one side edge 74 and a pair of spaced notches extending radially outwardly from the corners 76, 78 of a front edge 80 of the bore 42. Each of the notches 72, 76, 78 along with at least a portion of the bore 42 defines an opening for removably receiving the anvil end 56 of the rivet bar 58. As shown in FIGS. 9-11, the notches 72, 76, 78 of each of the three openings in the bore 42 facilitate sliding the tool 20 onto the rivet bar 58 in three different positions: toe portion facing to the left (FIG. 9), toe portion facing downwardly (FIG. 10), and toe portion facing to the right (FIG. 11).

The tool 20 may be secured relative to the rivet bar 58 in any of the above-described positions of the tool 20. For example, the lower leg 22 of the tool 20 may define a threaded opening for receiving a set screw (not shown) that is selectively tightened against the rivet bar 58 when the tool 20 is a selected position on the rivet bar.

Figure 12:
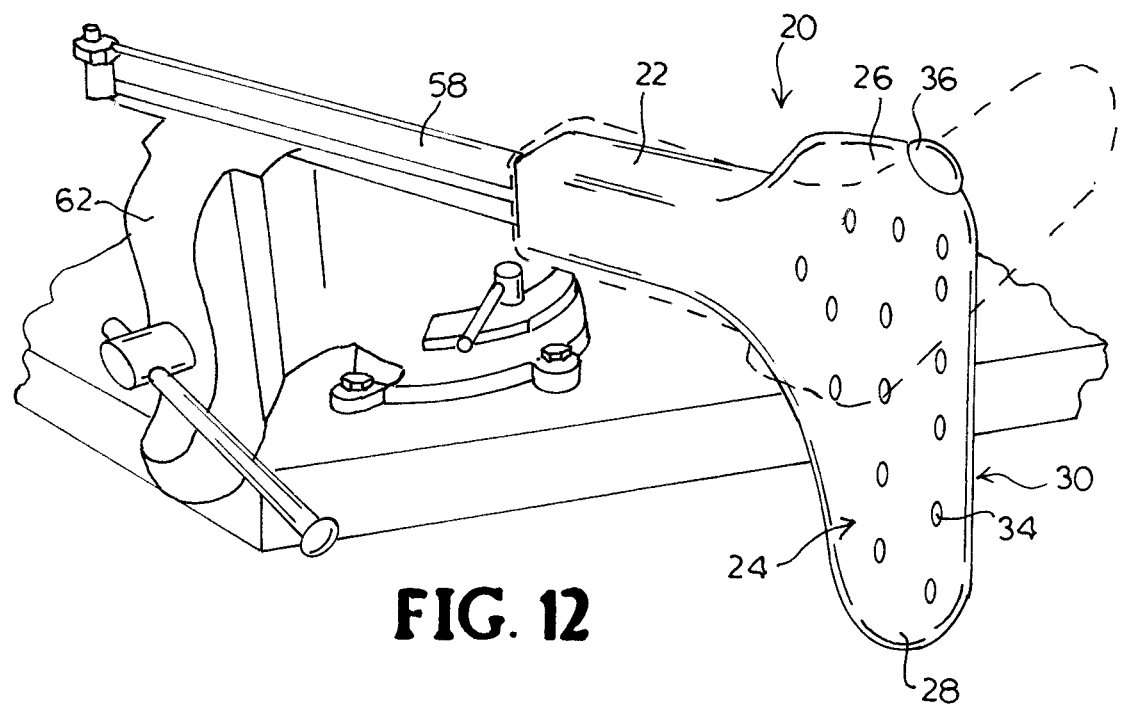
FIG. 12 is a perspective view of the modification tool in position on the rivet bar as shown in FIG. 3 with the rivet bar in a bench vice and a second position of the modification tool shown in phantom.

In use, the rivet bar 58 is secured in a machinist vice 62 so that the rounded surface of the anvil end 56 faces upward. The tool 20, 70 is slipped onto the anvil end 56 as described above. Two possible positions of the tool 20 relative to the rivet bar 58 are shown in FIG. 12, a position where the toe portion is directed downwardly and a position where the toe portion is directed to one side as shown in phantom. The peg 36, or pegs, is then inserted into one or more of the holes 34 in the outer surface 30 of the tool 20, 70 in the area, or areas, in need of reshaping in order to increase comfort or decrease undue pressure areas for the wearer. Once the peg 36 is in a preferred position, a surface of the orthosis 60 in the area of the irritation is heated for softening the plastic. The orthosis 60 is then placed over the tool 20, 70 in the same manner as a wearer would secure the orthosis 60 to the leg and foot. The hemispherical portion 38 of each peg 36 in the tool 20, 70 will thus engage the hot plastic of the orthosis 60 for pushing the inside surface outwardly or inwardly for creating a depression or reshaping. When cool and rigid, the orthosis will retain the depression or desired new shape, creating a better fit or space between the inside surface of the orthosis 60 and the location of the irritation of the wearer. Because the tool 20, 70 has a plurality of holes 34 spaced over the outer surface 30, any selected portions of the orthosis 60 may be modified as desired, depending on the areas of irritation affecting a wearer.

Figure 13:
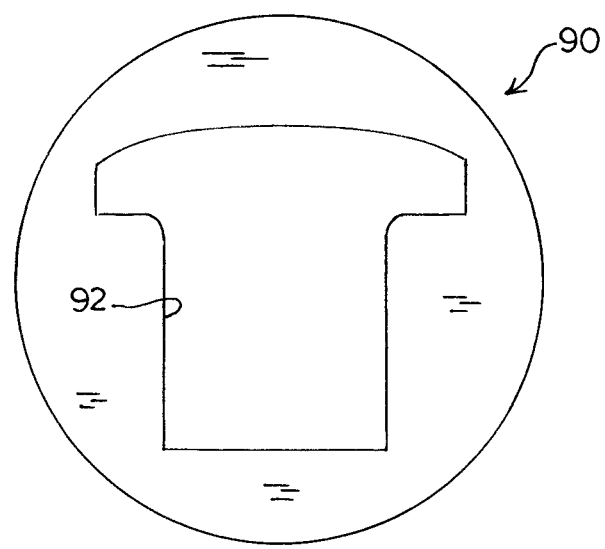
FIG. 13 is an elevational end view of a tool having an opening for receiving an anvil end of a rivet bar as shown in FIG. 3.

It is understood that, although the orthosis modification tool is described in detail herein with reference to exemplary embodiments of the tool 20, 70, the features of the tool 20, 70 may be applied to, and find utility in, other support-engaging tools. This aspect of the tool 20, 70 is shown in FIG. 13 as a sleeve 90 having an opening 92 configured to receive the anvil end 56 of the rivet bar 58. When used as described above, the supporting-engaging sleeve 90 may be combined with a tool in a wide variety of applications involving working or modifying a workpiece. Specifically, the sleeve 90 may be mounted to the tool, such as by insertion in an opening of the tool or otherwise securely fixing the sleeve 90 to the tool. The tool may then affixed to the rivet bar 58 or other corresponding structure by sliding the sleeve 90 and associated tool onto the rivet bar 58 as described hereinabove. Further, although the support-engaging feature is described in detail herein as embodied in an orthosis modification tool supported on a rivet bar, it is not intended to be so limited. The support-engaging feature may be used in other applications. Thus, the support-engaging structure has general applicability to any device wherein improvements in support and handling are desired.

Although the present invention has been shown and described in considerable detail with respect to only a few exemplary embodiments thereof, it should be understood by those skilled in the art that I do not intend to limit the invention to the embodiments since various modifications, omissions and additions may be made to the disclosed embodiments without materially departing from the novel teachings and advantages of the invention, particularly in light of the foregoing teachings. For example, although the modification tool is shown only with an ankle-foot orthosis, it is understood that the tool could be used with a knee-ankle-foot orthosis, a hip-knee-ankle-foot orthosis, ankle supports, foot orthotics or any other of a range of orthoses, supports, guards, and the like. Moreover, although the openings of the tool are illustrated as generally arcuate in shape, it is understood that the openings may be any shape necessary to accommodate a particular support member. Accordingly, I intend to cover all such modifications, omissions, additions and equivalents as may be included within the spirit and scope of the invention.

I claim:

1. An apparatus for mounting to a support for modifying an ankle-foot orthosis, the apparatus comprising:
    a tooling device formed in the shape of a lower leg and foot and having a plurality of holes spaced over an outer surface of the tooling device, the tooling device including
        a first portion having a longitudinal axis, and
        a second portion integral with the first portion and having a longitudinal axis substantially perpendicular to the longitudinal axis of the first portion, the second portion of the tooling device defining an opening for receiving the support; and
    a peg configured to be inserted into one or more holes of the tooling device.

2. The apparatus as recited in claim 1, wherein the peg comprises a body portion and a post depending from the body portion, the post configured to be received in the holes in the outer surface of the tooling device.

3. The apparatus as recited in claim 2, wherein the body portion of the peg has a convex outer surface.

4. A system for modifying an ankle-foot orthosis, the orthosis modification system comprising:
    a support;
    a tooling device formed in the shape of a lower leg and foot and having a plurality of holes spaced over an outer surface of the tooling device, the tooling device including
        a first portion having a longitudinal axis, and
        a second portion integral with the first portion and having a longitudinal axis substantially perpendicular to the longitudinal axis of the first portion, the second portion of the tooling device defining an opening for receiving the support; and
    a peg configured to be inserted into one or more holes of the tooling device.

5. The orthosis modification system as recited in claim 4, wherein the opening in the second portion of the tooling device is configured to non-rotatably receive the support.

6. The orthosis modification system as recited in claim 5, wherein the opening in the second portion of the tooling device is configured to non-rotatably receive the support in a plurality of positions of the tooling device relative to the support.

7. The orthosis modification system as recited in claim 4, wherein the peg comprises a body portion and a post depending from the body portion, the post configured to be received in the holes in the outer surface of the tooling device.

8. The orthosis modification system as recited in claim 7, wherein the body portion of the peg has a convex outer surface.

* * * * *